(12) United States Patent
Evans et al.

(10) Patent No.: US 7,271,256 B2
(45) Date of Patent: Sep. 18, 2007

(54) METHOD FOR PRODUCING CIRCULAR OR MULTIMERIC PROTEIN SPECIES IN VIVO OR IN VITRO AND RELATED METHODS

(75) Inventors: Thomas C. Evans, Somerville, MA (US); Ming-Qun Xu, Hamilton, MA (US)

(73) Assignee: New England Biolabs, Inc., Ipswich, MA (US)

( * ) Notice: Subject to any disclaimer, the term of this patent is extended or adjusted under 35 U.S.C. 154(b) by 706 days.

(21) Appl. No.: 09/937,070

(22) PCT Filed: Jan. 31, 2001

(86) PCT No.: PCT/US01/03147

§ 371 (c)(1),
(2), (4) Date: Jan. 29, 2002

(87) PCT Pub. No.: WO01/57183

PCT Pub. Date: Aug. 9, 2001

(65) Prior Publication Data

US 2003/0013148 A1    Jan. 16, 2003

Related U.S. Application Data

(60) Provisional application No. 60/180,319, filed on Feb. 4, 2000.

(51) Int. Cl.
*C07H 21/04* (2006.01)
*C07K 1/00* (2006.01)
*C07K 1/14* (2006.01)
*C07K 1/22* (2006.01)
*C12N 15/00* (2006.01)
*C12N 9/00* (2006.01)

(52) U.S. Cl. .................. 536/23.4; 435/69.1; 435/69.7; 435/183; 530/402; 530/412; 530/413

(58) Field of Classification Search ............... 435/69.7, 435/69.1, 183; 530/402, 412, 413, 350; 536/23.4
See application file for complete search history.

(56) References Cited

U.S. PATENT DOCUMENTS 5,834,247 A    11/1998   Comb et al. ............... 435/69.7
6,849,428 B1 *  2/2005   Evans et al. ............... 435/69.7

OTHER PUBLICATIONS

Evans et al. Protein trans-Splicing and Cyclization by a Naturally Split Intein from the dnaE Gene of Synechocystis Species PCC6803. (Mar. 31, 2000) J. Biol. Chem. 275(13): 9091-9094.*
Iwai et al. Cyclic Green Fluorescent Protein Produced in Vivo Using an Artificially Split Pl-Pful Intein from Pyrococcus furiosus. (May 11, 2001) J. Biol. Chem. 276(19): 16548-16554.*
Samyn, et al., FEBS Lett., 352(1): 87-90 (1994).
Tang, et al., Science, 286(5439): 498-502 (1999).
Tam and Lu, Protein Sci., 7(7): 1583-1592 (1998).
Romanovskis and Spatola, J. Pept. Res., 52(5): 356-374 (1998).
Camarero and Muir, J. Amer. Chem. Soc., 121: 5597-5598 (1999).
Valero, et al., J. Pept. Re., 53(1) 56-67 (1999).
Evans, et al., J. Biol. Chem., 274: 18359-18363 (1999).
Iwai and Pluckthun, FEBS Lett., 459: 166-172 (1999).
Perler, et al., Nucleic Acids Res., 22: 1125-1127 (1994).
Paulus, Chem. Soc. Rev., 27: 375-386 (1998).
Perler, Cell 92(1): 1-4 (1998).
Shao and Kent, Chem. Biol., 4(3): 187-194 (1997).
Xu and Perler, EMBO J. 15(19): 5146-5153 (1996).
Chong, et al., J. Biol. Chem., 271: 22159-22168 (1996).
Chong, et al., Gene, 192(2): 271-281 (1997).
Chong, et al., Nucleic Acids Res. 26(22): 5109-5115 (1998).
Evans, et al., Protein Sci., 7: 2256-2264 (1998).
Mathys, et al., Gene 231: 1-13 (1999).
Evans, et al., J. Biol. Chem., 274: 3923-3926 (1999).
Southworth, et al., Biotechniques, 27: 110-120 (1999).
Wood, et al., Nature Biotechnology, 17(9): 889-892 (1999).
Cotton, et al., J. Am. Chem. Soc. 121: 1100-1101 (1999).
Muir, et al., Proc. Natl. Acad. Sci. USA 95: 6705-6710 (1998).
Severinov and Muir, J. Biol. Chem. 273: 16205-16209 (1998).
Xu, et al., Proc. Natl. Acad. Sci. USA 96(2): 388-393 (1999).
Yamazaki, et al., J. Am. Chem. Soc. 120: 5591-5592 (1998).
Mills, et al., Proc. Natl. Acad. Sci. USA, 95(7): 3543-3548 (1998).
Southworth, et al., EMBO J., 17(4): 918-926 (1998).
Wu, et al., Biochim. Biophys. Acta, 1387: 422-432 (1998).
Otomo, et al., J. Biomol. NMR, 14(2): 105-114.
Otomo, et al., Biochemistry, 39(49): 16040-16044.
Wu, et al., Proc. Natl. Acad. Sci. USA, 95(16): 9226-9231 (1998).
Watanabe, et al., J. Bacteriol., 176: 4465-4472 (1994).
Shingledecker, et al., Gene, 207(2): 187-195 (1998).
Kent, S.B.H., Annu. Rev. Biochem., 57: 957-989 (1988).
Evans, et al., Biopolymers, 51(5): 333-342 (1999).
Noren, et al., Angewandte Chemie Int. Ed., 39: 450-466 (2000).
Duplay, et al., J. Biol. Chem. 259: 10606-10613 (1984).
Chang and Cohen, J. Bacteriol. 134: 1141-1156 (1978).
Scott, et al., Proc. Natl. Acad. Sci. USA 96: 13638-13643 (1999).

* cited by examiner

*Primary Examiner*—Kathleen Kerr Bragdon
*Assistant Examiner*—Holly Schnizer
(74) *Attorney, Agent, or Firm*—Harriet M. Strimpel (57) ABSTRACT

Methods are provided for intein mediated trans-splicing of immobilized polypeptides and for producing cyclic polypeptides in vivo or in vitro.

20 Claims, 6 Drawing Sheets

A. Intermolecular Trans-splicing

B. Intramolecular Trans-splicing

Cyclized Target Protein

METHOD FOR PRODUCING CIRCULAR OR MULTIMERIC PROTEIN SPECIES IN VIVO OR IN VITRO AND RELATED METHODS

CROSS REFERENCE

The present application is a 371 of international application No. PCT/US01/03147 filed Jan. 31, 2001, which gains priority from provisional application No. 60/180,319 filed Feb. 4, 2000, incorporated herein by reference.

BACKGROUND OF THE INVENTION

There are a number of modifications that proteins can undergo following translation. Some of the many post-translational modifications result in proteolytic processing or the covalent linkage of an important functional group to the protein. An interesting post-translational modification is the head-to-tail cyclization of a protein or peptide to form a continuous peptide backbone. Many of the naturally occurring circular peptides posses anti-bacterial activity, such as the AS-48 peptide (Samyn, et al., *FEBS Lett.*, 352(1) 87-90 (1994)). Also, these antibacterial peptides have been found in organisms as divergent as bacteria and primates (Samyn, et al., *FEBS Lett.*, 352(1) 87-90 (1994); Tang, et al., *Science*, 286(5439) 498-502 (1999)). One possibility for forming a cyclic protein species may be that the peptide or protein is more conformationally stable once its N- and C-termini have been constrained.

In addition to the naturally occurring cyclic peptides a number of synthetic techniques have been developed to generate synthetic circular peptides (Tam and Lu, *Protein Sci.*, 7(7) 1583-1592 (1998); Romanovskis and Spatola, *J. Pept. Res.*, 52(5) 356-374 (1998); Camarero and Muir, *J. Amer. Chem. Soc.*, 121 5597-5598 (1999); Valero, et al., *J. Pept. Res.*, 53(1) 56-67 (1999)). However, due to the limitations of total chemical synthesis it is difficult to generate synthetic cyclic peptides larger than 100 amino acids. This was circumvented using intein based technologies that allowed ribosomally synthesized proteins to cyclize in a head-to-tail fashion in vitro (Camarero and Muir, *J. Amer. Chem. Soc.*, 121 5597-5598 (1999); Evans, et al., *J. Biol. Chem.*, 274 18359-18363 (1999); Iwai and Pluckthun, *FEBS Lett.*, 459 166-172 (1999)). However, these procedures did not allow the cyclization of a protein or peptide in vivo for study in a living organism.

The in vitro cyclization of ribosomally synthesized proteins utilize the activity of protein splicing elements (termed inteins Perler, et al., *Nucleic Acids Res.*, 22 1125-1127 (1994)). Inteins, catalyze their own excision from a primary translation product with the concomitant ligation of the flanking protein sequences (reviewed in Paulus, *Chem. Soc. Rev.*, 27:375-386 (1998), Perler, *Cell* 92(1)1-4 (1998) and Shao and Kent, *Chem. Biol.* 4(3):187-194 (1997)). Inteins catalyze three highly coordinated reactions at the N- and C-terminal splice junctions (Xu and Perler, *EMBO J.* 15(19): 5146-5153 (1996) and Chong, et al., *J. Biol. Chem.*, 271: 22159-22168 (1996)): 1) an acyl rearrangement at the N-terminal cysteine or serine; 2) a transesterification reaction between the two termini to form a branched ester or thioester intermediate; and 3) peptide bond cleavage coupled to cyclization of the intein C-terminal asparagine to free the intein. Inteins have been engineered to be versatile tools in protein purification (Chong, et al., *Gene*, 192(2) 271-281 (1997), Chong, et al., *Nucleic Acids Res.* 26(22):5109-5115 (1998), Evans, et al., *Protein Sci.*, 7:2256-2264 (1998), Mathys, et al., *Gene* 231:1-13 (1999), Evans, et al., *J. Biol. Chem.*, 274:3923-3926 (1999), Southworth, et al., *Biotechniques*, 27:110-120 (1999) and Wood, et al., *Nature Biotechnology*, 17(9):889-892 (1999)), protein ligation (Evans, et al., *Protein Sci.*, 7:2256-2264 (1998), Mathys, et al., *Gene* 231:1-13 (1999), Evans, et al., *J. Biol. Chem.*, 274:3923-3926 (1999), Southworth, et al., *Biotechniques*, 27:110-120 (1999), Cotton, et al., *J. Ant. Chem. Soc.* 121:1100-1101 (1999), Muir, et al., *Proc. Natl. Acad. Sci. USA*. 95:6705-6710 (1998), Severinov and Muir, *J. Biol. Chem.* 273: 16205-16209 (1998), and Xu, et al., *Proc. Natl. Acad. Sci. USA* 96(2):388-393 (1999)) as well as in the aforementioned formation of cyclic proteins and peptides (Evans, et al., *J. Biol. Chem.* 274:18359-18363 (1999), Iwai and Pluckthun, *FEBS Lett* 459:166-172 (1999) and Camarero and Muir, *J. Amer. Chem. Soc.*, 121:5597-5598 (1999)). Limitations of these intein technologies include the necessity of generating an N-terminal cysteine and/or C-terminal thioester intermediate in vitro for ligation or cyclization, the need to perform extra purification steps to separate unligated reactants from the ligation products and the requirement of a denaturant to permit in vitro trans-splicing reactions (Yamazaki, et al., *J. Am. Chem. Soc.* 120:5591-5592 (1998), Mills. et al., *Proc. Natl. Acad. Sci. USA*, 95(7):3543-3548 (1998), and Southworth, et al., *EMBO J.*, 17(4):918-926 (1998)).

In addition to the cis-splicing inteins and those engineered to trans-splice (Yamazaki, et al., *J. Am. Chem. Soc.* 120: 5591-5592 (1998), Wu, et al., *Biochim. Biophys Acta*, 1387: 422-432 (1998), Mills, et al., *Proc. Natl. Acad. Sci. USA*, 95(7):3543-3548 (1998), Otomo, et al., *J. Biomol. NMR*, 14(2):105-114, Otomo, et al. *Biochemistry*, 39(49):16040-16044, and Southworth, et al., *EMBO J.*, 17(4):918-926 (1998)), a naturally-occurring split intein was recently identified in the dnaE gene encoding the catalytic subunit of DNA polymerase III of *Synechocystis* sp. PCC6803 (Wu, et al., *Proc. Natl. Acad. Sci. USA*, 95(16):9226-9231 (1998)). The N-terminal half of DnaE, followed by a 123-amino acid intein sequence, and the C-terminal half, preceded by a 36-amino acid intein sequence, are encoded by two open reading frames located more than 745 kilobases apart in the genome. When co-expressed in *E. coli*, the two DnaE-intein fragments exhibited protein trans-splicing (Wu, et al., *Proc. Natl. Acad. Sci. USA*, 95(16):9226-9231 (1998)).

Accordingly, it would be desirable to utilize intein technology in developing methods for producing circular or multimeric protein species in vivo or in vitro. Such methods would permit the formation of cyclic polypeptides in new hosts, facilitate the separation of products from reactants when ligating proteins for isotopic labeling, and allow the generation of cyclic polypeptides that are sensitive to reducing agents.

SUMMARY OF THE INVENTION

The abbreviations used herein are:

"*Ssp* DnaE intein" means a naturally split intein from the dnaE gene of *Synechocystis* sp. PCC6803;

"DnaE(N)" means the N-terminal 123 amino acid residues of the *Ssp* DnaE intein;

"DnaE(C)" means the C-terminal 36 amino acid residues of the *Ssp* DnaE intein;

"MBP" means maltose binding protein;

"CBD" means chitin binding domain;

"Fxa" means factor Xa;

"ITS" means intramolecular trans-splicing.

In accordance with one embodiment of the present invention, there is provided a method for producing a circular or multimeric protein species in vivo or in vitro. The steps comprising the in vivo cyclization or multimerization reaction consists of fusing the C-terminal splicing domain of a protein splicing element (an intein) to the N-terminus of the target protein and the N-terminal splicing domain of an intein to the C-terminus of the same target protein and expressing the fusion protein in the desired organism at the temperature permissive for intein splicing. Cyclization occurs when the two splicing domains from the same target protein interact and splice whereas multimerization occurs if the two splicing domains from two different target proteins interact and splice.

The intein splicing domains are also referred to herein as intein fragments. The intein fragments are chosen so that they represent complementary trans-splicing domains. These complementary intein fragments could be chosen from the known trans-splicing inteins (Yamazaki, et al., *J. Am. Chem. Soc.* 120:5591-5592 (1998), Wu, et al., *Biochim. Biophys. Acta*, 1387:422-432 (1998), Mills, et al., *Proc. Natl. Acad. Sci. USA*, 95(7):3543-3548 (1998), Wu, et al., *Proc. Natl. Acad. Sci. USA*, 95(16):9226-9231 (1998), Otomo, et al., *J. Biomol. NMR*, 14(2):105-114, Otomo, et al., *Biochemistry*, 39(49):16040-16044, and Southworth, et al., *EMBO J.*, 17(4):918-926 (1998)). The intein fragments used in the present study were the N-terminal 123 amino acids and the 36 C-terminal amino acids of the of the Ssp DnaE intein, respectively.

This intein based technology allows naturally occurring circular proteins to be expressed in organisms that are not the native host. Furthermore, this technology permits a wide range of circular proteins, including those not found in nature to be expressed in such organisms.

In vitro cyclization also involves fusing the C-terminal splicing domain of an intein to the N-terminus of the target protein and the N-terminal splicing domain of an intein to the C-terminus of the same target protein as described above. However, expression of the fusion protein in the desired organism is carried out under conditions that are not permissive for intein splicing. Also, one or both intein splicing domains may carry an affinity tag that allows immobilization on an affinity resin.

The present invention is exemplified by, though not limited to, the intein found in the dnaE gene of *Synechocystis* sp. PCC6803 (Ssp DnaE intein). The first step in the in vitro cyclization reaction is the generation of the full length precursor protein, either by ribosomal synthesis or by total chemical synthesis. The full length precursor protein is then immobilized on a solid support, such as a chitin resin. Protein cyclization occurs when the resin containing the bound protein is equilibrated at the appropriate temperature and pH to allow splicing to proceed. As described above for the in vivo case, cyclization occurs if the two splicing domains from the same target protein interact and splice whereas multimerization occurs if the two splicing domains from two different target proteins interact and splice. Following the trans-splicing reaction to generate the cyclic protein species the final products were eluted from the chitin resin. This method is unlike previous intein based in vitro cyclization techniques, referenced above, and may be used to circularize proteins that are sensitive to the reducing agents used in the other procedures or are not amenable to use with other inteins.

The present invention also describes a method for ligating two protein fragments on-column and separating away the reactants by elution from the affinity resin. The steps involved comprise fusing target protein 1 to a C-terminal intein splicing domain while target protein 2 is fused to an N-terminal intein splicing domain.

An affinity domain can be fused to both or either of the N- and C-terminal intein splicing domains so that the N- and C-terminal protein fusion molecules can be immobilized on an affinity resin. The affinity domain exemplified herein is the chitin binding domain from *B. circulans* (Watanabe, et al., *J. Bacteriol.*, 176:4465-4472 (1994)). Following the generation of the precursor proteins in the present invention they are applied to a chitin resin The immobilized proteins are ligated together when favorable conditions exist to permit the complementary intein fragments from separate molecules to undergo the trans-splicing reaction.

Following trans-splicing the ligated protein products were no longer fused to the intein fragments or the affinity domain and so these products were isolated by eluting it from the chitin resin. In contrast, the unused reactants remained bound This permits the localization of the ligation reaction and overcomes many of the disadvantages and problems of the previous technologies noted above. Specifically, the present invention allows the facile separation of the ligated protein species from the unused reactants and the use of inteins such as the Ssp DnaE intein eliminates the need for the denaturant treatment step to permit the trans-splicing reaction.

The present invention also relates to a method for controlling cleavage at the intein splice junctions. In this embodiment, a protein is fused to the N-terminal intein splicing domain. This fusion protein may or may not be purified. Cleavage of the fusion protein is induced by the addition of the complementary C-terminal splicing domain, that may or may not contain a mutation to block any potential splicing activity. Alternatively, a protein is fused to the C-terminal intein splicing domain. This fusion may or may not be purified. Cleavage is induced by the addition of the N-terminal intein splicing domain. In both of the above instances, the cleavage reaction may be accelerated using reagents or conditions that increase the rate of cleavage, such as thiol reagents, pH, or temperature. This mechanism of controllable cleavage has been termed trans-cleavage.

BRIEF DESCRIPTION OF THE DRAWINGS

FIG. 2A, Cis-splicing activity of the Ssp DnaE intein investigated by expression of the MBP-DnaE-CBD fusion (MEB) protein in *E. coli*. Lane 1, uninduced crude cell extract. Lane 2, crude cell extract following induction at 15° C. overnight. The MEB precursor (68 kDa), the splicing products MB (50 kDa) and E (18 kDa) and the cleavage products M (43 kDa) and EB (25 kDa) are visible. Lane 3, crude cell extract after a 2 hour induction at 37° C. Lane 4. Crude cell extract after a 2 hour induction at 37° C. followed by overnight incubation at 15° C.

FIG. 2B, The cis-splicing activity of the Ssp DnaE intein in vivo with mutated extein residues. Lane 1, in vivo splicing activity with 2 native N-extein and 3 native C-extein residues (pMEB-N2). The splicing of the Ssp DnaE intein with 5 native N-extein residues and 1 (pMEB8-C1, lane 2), 2 (pMEB8-C2, lane 3) or 3 native C-extein residues (pMEB8-C3, lane 4).

FIG. 2C, The Ssp DnaE intein in vivo trans-splicing activity investigated by co-expression of the MBP-DnaE(N) (57 kDa) and the DnaE(C)-CBD (10 kDa) fusion proteins. Lane 1, uninduced crude cell extract. Crude cell extract after induction of protein expression at 15° C. (Lane 2), at 37° C. (Lane 3) and at 37° C. followed by incubation with shaking at 15° C. (Lane 4) all displayed precursor (MEB), spliced product (M) and cleavage product (M). Lane 5, induction of protein expression with ME(N), but not E(C)B, displayed no detectable splicing or cleavage. All samples were analyzed by Coomassie Blue stained 12% SDS-PAGE gels.

FIG. 3A, Intermolecular trans-splicing (ITS). The association of the N-terminal and C-terminal Ssp DnaE intein fragments, DnaE(N) and DnaE(C), respectively, aligns the two splice junctions for the fusion of the N-and C-extein sequences. The splicing reaction presumably occurs via the same splicing pathway as the cis-splicing pathway proposed previously (Xu and Perler, EMBO J., 15(19):5146-5153 (1996) and Chong, et al., J. Biol. Chem. 271:22159-22168 (1996)). Cleavage at the N-terminal splice junction can occur by hydrolysis or nucleophilic attack of the thioester bond formed at the C-terminus of the N-extein.

FIG. 3B, Intramolecular trans-splicing (ITS). A target protein is sandwiched between the intein C-terminal segment (36 amino acids) and the intein N-terminal segment (123 amino acids). Splicing joins the N-terminus of the target protein to its own C-terminus through a peptide bond. The presence of a chitin binding domain (CBD) fused to the C-terminus of the intein N-terminal segment facilitated purification of the precursor protein and the subsequent in vitro cyclization reaction on chitin resin.

FIG. 4 is a gel depicting the in vitro trans-splicing of the Ssp DnaE intein as well as the trans-cleavage reaction.

FIG. 4A, 10-20% SDS-PAGE gel of peptide induced splicing and cleavage of MBP-DnaE(N)-CBD (ME(N)B). Lane 1, amylose purified ME(N)B (64 kDa). Lane 2, ME(N) B, 1 mg/mL, following overnight incubation with the splicing peptide (Splice-pep, 500 :M). The cleavage product (M) and spliced product (M-CFNK*) co-migrate at 43 kDa. Lane 3, ME(N)B, 1 mg/mL, after overnight incubation with the cleavage peptide (Cleav-pep, 500 :M). Both Splice-pep and Cleav-pep are based on the C-terminal fragment of the Ssp DnaE intein as described in the Example III and Example IV.

FIG. 4B, trans-splicing of MBP-DnaE(N)-CBD (ME(N) B) and CBD-DnaE(C)-T4 ligase (BE(C)L) examined by 12% SDS-PAGE. Lane 1, crude cell extract after induction of ME(N)B expression. Lane 2, ME(N)B following purification over an amylose column. Lane 3, ME(N)B that was bound to chitin beads and eluted with SDS. The chitin binding domain (CBD) permits binding to a chitin resin Lane 4, crude cell extract after induction of BE(C)L expression. Lane 5, chitin bound BE(C)L that was removed by treatment with SDS. Lane 6, incubation of amylose-purified ME(N)B and chitin bound BE(C)L at 4° C. for 16 hours followed by elution of the chitin resin with SDS. The fusion proteins ME(N)B and BE(C)L were bound to separate batches of chitin beads and the chitin bound proteins were mixed followed by elution of the beads with SDS after incubation at 4° C. (lane 7), 16° C. (lane 8) or 37° C. (lane 9) for 16 hours. Lane 10, the supernatant from the chitin bead mixture described in lane 8. Note that the spliced product (ML) is free in solution while the reactants remain bound to the chitin heads Lane 11, Factor Xa (Fxa) treatment (1:100 FXa:ML) of the supernatant fraction. M, MBP (43 kDa). L, T4 DNA ligase (58 kDa).

FIG. 5A, in vivo protein cyclization. Lane 1, uninduced crude cell extract. Lane 2, crude cell extract following induction at 15° C. contains the precursor DnaE(C)-MBP-DnaE(N)-CBD (E(C)ME(N)B, 65 kDa), cyclic MBP (c-MBP, 47 kDa), linear MBP (l-MBP, 43 kDa), the DnaE (C)-MBP (E(C)M, 45 kDa), and DnaE(N)-CBD (E(N)B, 23 kDa). Lane 3, clarified cell extract from Lane 2 following passage over an amylose column. Note that the cyclic maltose binding protein (MBP) binds to amylose. Lane 4, proteins eluted from amylose resin. Lane 5, the eluted sample incubated with Factor Xa (1:100 FXa:MBP). FXa treatment also resulted in the release of a 45 kDa species corresponding to E(C)M.

FIG. 5B, in vitro protein circularization. Lane 1, uninduced cell extract. Lane 2, crude cell extract following induction at 37° C. Lane 3, clarified cell extract following passage over a chitin column. Lane 4, proteins eluted from the chitin column following incubation at 23° C. for 16 hours. Lane 5, incubation of the chitin eluted sample with Factor Xa (1:100 FXa:MBP). All reactions were performed as described in Example V and were analyzed on a 12% SDS-PAGE gel.

DETAILED DESCRIPTION OF THE INVENTION

The cyclization and ligation methods of the present invention are based on the discovery that split inteins are capable of trans-splicing either in vitro or in vivo (U.S. Pat. No. 5,834,247; Mills, et al., Proc. Natl. Acad. Sci. USA, 95(7) 3543-3548 (1998); Otomo, et al., J. Biomol. NMR, 14(2) 105-114 (1999); Shingledecker, et al., Gene, 207(2) 187-195 (1998); Southworth, et al., EMBO J., 17(4) 918-926 (1998); Yamazaki, et al., J. Am. Chem. Soc., 120 5591-5592 (1998))

The ligation procedure disclosed herein utilizes a split protein splicing element, an intein (Perler, et al., Nucleic Acids Res., 22 1125-1127 (1994)) to join the N- and C-termini of the same or separate protein species. Previously, the ligation of the N- and C-termini of separate protein sequences was described using an intein (CIVPS) that was artificially split (U.S. Pat. No. 5,834,247; Mills, et al., Proc. Natl. Acad. Sci. USA, 95(7) 3543-3548 (1998); Otomo, et al., J. Biomol. NMR, 14(2) 105-114 (1999); Shingledecker, et al. Gene, 207(2) 187-195 (1998): Southworth. et al., EMBO J., 17(4) 918-926 (1998), Yamazaki, et al., J. Am. Chem. Soc., 120 5591-5592 (1998). However, the present invention describes how a split intein can be used to fuse two protein segments on a solid support. The present invention relies on the generation of precursor proteins composed of complementary intein fragments and the desired target proteins.

The first step in the ligation of proteins on a solid support is the generation of the necessary precursor proteins comprising the intein fragment fused to the target protein at the genetic level followed by expression of the gene. For example, in order to create a fusion protein of a C-terminal intein fragment fused to the N-terminus of a first target protein (target protein 1), the gene encoding the C-terminal intein fragment is cloned in frame to the gene encoding the target protein 1. The genes are arranged so that the C-terminus of the C-terminal intein fragment is fused to the N-terminus of target protein 1.

Alternatively, the precursor protein comprising an N-terminal intein fragment fused to a second target protein (target protein 2) is created by cloning the gene encoding the N-terminal intein fragment in frame to the gene encoding target protein 2. Specifically, the genes are arranged so that the C-terminus of target protein 2 is fused in-frame with the N-terminus of the N-terminal intein fragment. In either case the new gene fusion is placed into a context that permits it's transcription and translation to result in the production of the desired fusion protein. For example, the fusion genes could be cloned into an E. coli expression vector such as that described previously for intein purification vectors (Chong, et al., Gene 192(2):271-281 (1997); (Evans, et al., Protein Sci., 7:2256-2264 (1998)), but could be any expression vector system. In addition to the generation of ribosomally synthesized precursor proteins as described above, the same fusion proteins could be chemically synthesized using standard procedures (reviewed in Kent, S. B. H., Annu. Rev. Biochem, 57:957-989 (1988).

The intein fragments are chosen to be complementary trans-splicing domains. For example, the complementary intein fragments could be chosen from the known trans-splicing inteins, such as the Ssp DnaE Intein, Ssp DnaE intein, Mtu RecA intein, Psp Pol-1 intein, PI-pfuI intein and PI-pfuII intein (Yamazaki, et al., J. Am. Chem. Soc. 120: 5591-5592 (1998), Wu, et al., Biochim. Biophys, Acta, 1387:422-432 (1998), Mills, et al., Proc. Natl. Acad. Sci. USA, 95(7):3543-3548 (1998), Wu, et al., Proc. Natl. Acad. Sci. USA, 95(16):9226-9231 (1998), Otomo, et al., J. Biomol NMR, 14(2):105-114, Otomo, et al., Biochemistry, 39(49): 16040-16044, and Southworth, et al., EMBO J., 17(4):918-926 (1998)). The intein fragments used in the present study were the N-terminal 123 amino acids and the 36 C-terminal amino acids of the of the Ssp DnaE intein, respectively.

An affinity domain can be fused to both or either of the N- and C-terminal intein splicing domains so that the N- and C-terminal protein fusion molecules can be immobilized on a solid support such as an affinity resin. The affinity domain exemplified herein is the chitin binding domain from B. circulans (Watanabe, et al., J. Bacteriol., 176:4465-4472 (1994)). Following the generation of the precursor proteins they are applied to a solid support where they are immobilized. The nature of the solid support will depend on the goals of the experiment, but may be an affinity column. The solid support in the present disclosure is a chitin resin, but could be any support such as microtiter plates, beads, or materials used in biochips, such as glass wafers.

The immobilized proteins are ligated together when favorable conditions exist to permit the complementary intein fragments from separate molecules to undergo the trans-splicing reaction. Favorable conditions include the proper salt concentration, pH, temperature, or the presence of a molecule, such as a reducing agent, that facilitates the splicing reaction. The conditions that favor trans-splicing can be elucidated for the intein fragments being used by directly testing its performance in vitro in a variety of conditions. The design of these experiments can be as described previously for trans-splicing inteins (Yamazaki, et al., J. Am. Chem. Soc. 120:5591-5592 (1998), Wu, et al., Biochim. Biophys. Acta, 1387:422-432 (1998), Mills, et al., Proc. Natl. Acad. Sci. USA, 95(7):3543-3548 (1998), Wu, et al., Proc. Natl. Acad. Sci. USA, 95(16):9226-9231 (1998), Otomo, et al., J. Biomol. NMR, 14(2):105-114, Otomo, et al., Biochemistry, 39(49):16040-16044, and Southworth, et al., EMBO J., 17(4):918-926 (1998)). For example, in the present disclosure the Ssp DnaE intein was found to trans-splice less efficiently at 37° C. than at 15° C. and was less active at pH>10 than at a neutral pH.

Following trans-splicing the ligated protein products are no longer fused to the intein fragments or the affinity domain and so these products can be isolated by eluting it from the solid support. In contrast, the unused reactants remain bound. This permits the localization of the ligation reaction and overcomes many of the disadvantages and problems of the previous technologies noted above. Specifically, the present invention allows the facile separation of the ligated protein species from the unused reactants and the use of the Ssp DnaE intein eliminates the need for the denaturant treatment step to permit the trans-splicing reaction.

The in vivo cyclization reaction of the instant invention begins with the in-frame fusion of the gene encoding the C-terminal splicing domain of an intein to the gene encoding the target protein and the in-frame fusion of the gene encoding the N-terminal splicing domain of an intein to the gene encoding the same target protein. The gene is arranged so that following translation the C-terminus of the C-terminal splicing domain is fused to the N-terminus of the target protein and the N-terminus of the N-terminal splicing domain is fused to the C-terminus of the target protein. This precursor protein is represented as Intein$_C$-target-Intein$_N$. The intein used in the present disclosure is the Ssp DnaE intein, but could be any complementary intein fragments as described above.

The Intein$_C$-target-Intein$_N$ fusion gene is placed into a context that permits its transcription and translation to result in the production of the desired precursor protein. For example, the gene could be cloned into an E. coli expression vector such as those described previously (Chong, et al., Gene 192(2):271-281 (1997); Evans, et al., Protein Sci., 7:2256-2264 (1998). The organisms intracellular environment and the organisms growth conditions should be favorable for trans-splicing. The conditions that favor trans-splicing can be elucidated for the intein fragments being used by directly testing its trans-splicing activity in the desired organism or by testing its performance in vitro in a variety of conditions. The design of these experiments can be as described previously for trans-splicin, interns (Yamazaki, et al., J. Am. Chem. Soc. 120:5591-5592 (1998), Wu, et al., Biochim. Biophys. Acta, 1387:422432 (1998), Mills, et al., Proc. Natl. Acad. Sci. USA, 95(7):3543-3548 (1998), Wu, et al., Proc. Natl. Acad. Sci. USA, 95(16):9226-9231 (1998), Otomo, et al., J. Biomol. NMR, 14(2):105-114, Otomo, et al., Biochemistry, 39(49):16040-16044, and Southworth, et al., EMBO J., 17(4):918-926 (1998)). For example, in the present disclosure the Ssp DnaE intein was found to trans-splice less efficiently at 37° C. than at 15° C. temperatures. In this case, the E. coli cells expressing the Intein$_C$-target-Intein$_N$ precursor should be grown at 15° C. to facilitate trans-splicing and thereby the cyclization reaction.

The cyclization reaction itself occurs when the trans-splicing of the inteins in the Intein$_C$-target-Intein$_N$ precursor generates a peptide bond between the N- and C-terminus of the target protein. This allows circular proteins to be produced in organisms that may not normally be able to do so.

The in vivo multimerization reaction of the present invention also begins with an Intein$_C$-target-Intein$_N$ gene fusion. However, following expression of the fusion protein the two complementary intein splicing domains from separate Intein$_C$-target-Intein$_N$ precursor proteins initiate the splicing reaction to ligate the two or more target proteins together.

The ratio of the intramolecular reaction, cyclization, to the intermolecular reaction, multimerization, may be controlled by engineering the target protein. For example if the N- and C-terminus of the target protein cannot come into close proximity. then the cyclization reaction will not be favored and multimerization should predominate. However, if the N- and C-terminus of the target protein are spatially close to one another, then the cyclization reaction should predominate. The determination of the proximity of the N- and C-terminus of the target protein can be estimated based on X-ray or NMR structural data. However, the exact determination of whether the N- and C-terminus of a target protein can be brought together and ligated by trans-splicing will need to be determined experimentally. Should it be discovered that the target protein does not cyclize, then an extra amino acid linker can be added to facilitate the cyclization reaction. The number of amino acids needed in the linker to ligate the ends of the target protein may be determined by adding a linker of increasing length until cyclization occurs, as determined experimentally. Alternatively, if X-ray or NMR structural data is available, then a starting point for the length of the linker would be to determine the distance between the ends of the target protein. This distance would be converted into a trial length for the linker by estimating the number of amino acids needed to span that distance. However, the final determination if the linker is of the proper number of amino acids is by experimental verification of the production of the desired cyclic protein.

The in vitro cyclization reaction of the present invention begins with the Intein$_C$-target-Intein$_N$ gene fusion arranged as described above. The gene is placed into a context that permits its expression to generate the precursor protein as described above. In this example, however, the intracellular environment of the host organism or its growth conditions should not favor the trans-splicing reaction.

This is to prevent the cyclization reaction due to trans-splicing from occurring in vivo. In the present description, the Ssp DnaE intein did not splice proficiently at 37° C. and so induction of protein expression was performed at 37° C. Conditions which are not favorable for intein splicing can be determined for the intein being used by performing experiments as described above for the determination of favorable splicing conditions. In addition to the generation of ribosomally synthesized precursor proteins, the same fusion protein could be chemically synthesized using standard procedures (reviewed in Kent, S. B. A, Annu. Rev. Biochem., 57:957-989 (1988)).

The full length fusion protein is then purified on a solid support using an affinity tag. The solid support used in the present disclosure is a chitin resin, but could be any solid support such as microtiter plates, beads, or materials used in biochips such as glass wafers. Furthermore, while the affinity tag used in the present invention was a chitin binding domain (Watanabe, et al., *J. Bacteriol.*, 176 4465-4472 (1994)), any affinity tag such as maltose binding protein, His tag, Flag tag or the cellulose binding domain could be used. The affinity tag can be present on none, both, or one of the intein splicing domains.

Following immobilization of the full length fusion protein on an affinity resin any unbound protein can be washed away. Cyclic protein is generated by equilibrating the solid support at conditions that favor trans-splicing of the intein. In the present invention the solid support, a chitin resin, with the immobilized Intein$_C$-target-Intein$_N$ precursor protein was allowed to equilibrate to room temperature, which is a temperature that was determined experimentally to be favorable for trans-splicing of the Ssp DnaE intein The optimal conditions for the intein being used can be determined experimentally as described above. Trans-splicing of the intein fragments results in a cyclic protein which can be eluted from the solid support.

Furthermore, as described for the in vivo case, it is possible to generate multimers consisting of repeating units of the target protein. As described above these are generated by an intermolecular reaction of the Intein$_C$-target-Intein$_N$ precursor proteins. The conditions necessary are the same as for in vitro cyclization with the exception that the intermolecular reaction should be optimized over the intramolecular reaction. This needs to be determined experimentally, but can be carried out as described for the in vivo cyclization reaction.

The intein based trans-cleavage method of the present invention begins with the fusion of a target protein to the N-terminal intein splicing domain. Specifically the C-terminus of the target protein is fused to the N-terminus of the intein splicing domain. This Intein$_N$-target protein fusion may or may not be purified. Because only a portion of the intein is present no unwanted intein mediated cleavage occurs in vivo or in vitro. Also, the precursor can be stored in the presence of reagents that induce cleavage in other intein fusions or in conditions that promote full length intein cleavage. Cleavage is initiated by adding the C-terminal intein splicing domain. This may be synthetic or ribosomally synthesized. In the present disclosure both a native and a modified C-terminal intein domain were used to induce cleavage of the peptide bond at the N-terminus of the complementary intein fragment, the N-terminal intein splicing domain. Mutations that may be made to block intein splicing activity, but which can still allow cleavage of certain peptide bonds adjacent to the intein have been described previously (Chong, et al., *Gene*, 192(2):271-281 (1997), Chong, et al., *Nucleic Acids Res.* 26(22):5109-5115 (1998), Evans, et al., *Protein Sci.*, 7:2256-2264 (1998), Mathys, et al., *Gene* 231:1-13 (1999), Evans, et al., *J. Biol. Chem.*, 274:3923-3926 (1999), Southworth, et al., *Biotechniques*, 27:110-120 (1999) and Wood, et al., *Nature Biotechnology*, 17(9):889-892 (1999) and reviewed in Evans, et al., *Biopolymers*, 51(5):333-342 (1999) and Noren, et al., *Angewandte Chemie Int. Ed.*, 39:450-466 (2000)). Alternatively, the target protein could be fused to the C-terminal intein splicing domain. Specifically, the N-terminus of the target protein is fused to the C-terminus of the intein splicing domain. Cleavage is induced by adding the N-terminal splicing domain with or without a mutation to block splicing activity. In either of the above cases, the precursor protein may or may not be purified. Purification would be simplified using an affinity domain attached to the intein tag. The precursor would be immobilized on the appropriate affinity column and unbound proteins could be washed away. Cleavage would be initiated by adding the appropriate intein splicing domain. The trans-cleavage reaction could be accelerated using reagents or conditions known to induce or increase the rate of cleavage in other inteins, for example thiol reagents, pH, or temperature (Chong, et al., *Gene*, 192(2):271-281 (1997), Chong, et al., *Nucleic Acids Res.* 26(22):5109-5115 (1998), Evans, et al., *Protein Sci.*, 7:2256-2264 (1998), Mathys, et al., *Gene* 231:1-13 (1999), Evans, et al., *J. Biol. Chem.*, 274:3923-3926 (1999), Southworth, et al., *Biotechniques*, 27:110-120 (1999) and Wood, et al., *Nature Biotechnology*, 17(9):889-892 (1999) and reviewed in Evans, et al., *Biopolymers*, 51(5):333-342 (1999) and Noren, et al., *Angewandte Chemie Int. Ed.*, 39:450-466 (2000)).

The present invention is further illustrated by the following Examples. These Examples are provided to aid in the understanding of the invention and are not construed as a limitation thereof.

The references cited above and below are herein incorporated by reference.

EXAMPLE I

Creation of Vectors pMEB1, pMEB2, pMEB3 for cis-Splicing Studies:

Construction of Plasmids-pMEB1 was constructed by replacing the Sce VMA intein in pMYB129 (Chong, et al., *Gene* 192(2):271-281 (1997)) with the Ssp DnaE intein sequence spanning residues 5-123 to create a fusion gene composed of *E. coli* maltose-binding protein (MBP) (Duplay, et al., *J. Biol. Chem.* 259:10606-10613 (1984)), the Ssp DnaE intein (residues 5-123) and the Bacillus circulans chitin binding domain (CBD) (Watanabe, et al., *J. Bacteriol.* 176:4465-4472 (1994)). The Ssp DnaE intein fragment was amplified from plasmid pDnaE-C209 with primers 5'-TFFG-GTACCCGAAATTTTAACCGTTGAG-3' (SEQ ID NO:1) and 5'-GGCTCTTCCTTTAATTGTCCCAGCGTCAAG-3' (SEQ ID NO:2). The N-terminal splice junction sequence, containing the flanking 5 native N-extein residues and the 5 intein N-terminal residues, was inserted between maltose binding protein (MBP) and the intein coding regions by linker insertion into the XhoI and KpnI sites in pMEB1 to create pMEB2. The linker was formed by annealing oligonucleotides, 5'-TCGAGAAATTTGCTGAATATTGCCT-GTCT TTTGGTAC-3' (SEQ ID NO:3) and 5'-CAAAAGA-CAGGCAATATTCAGCAA ATTTC-3' (SEQ ID NO:4).

The DNA sequence encoding the C-terminal 36 amino acid residues and the first 3 C-extein residues (5'-ATGGT-TAAAGTTATCGGTCGTAGATCTCTGGG CGTG-CAGCGCATCTITGATATCGGTCTGCCG-CAGGACCATAACTTTCTG CTAGCCAACGGCGCTATCGCTGCTAACT-GCTTTAACAAATCC-3' (SEQ ID NO:5)) was inserted into pMEB2 to create pMEB3 which expresses a fusion protein (MEB) composed of maltose binding protein (MBP), the full length Ssp DnaE intein (residues 1-159) with 5 native extein residues at its N-terminus and 3 native residues at its C-terminus, and the chitin binding domain (CBD).

Figure 1:
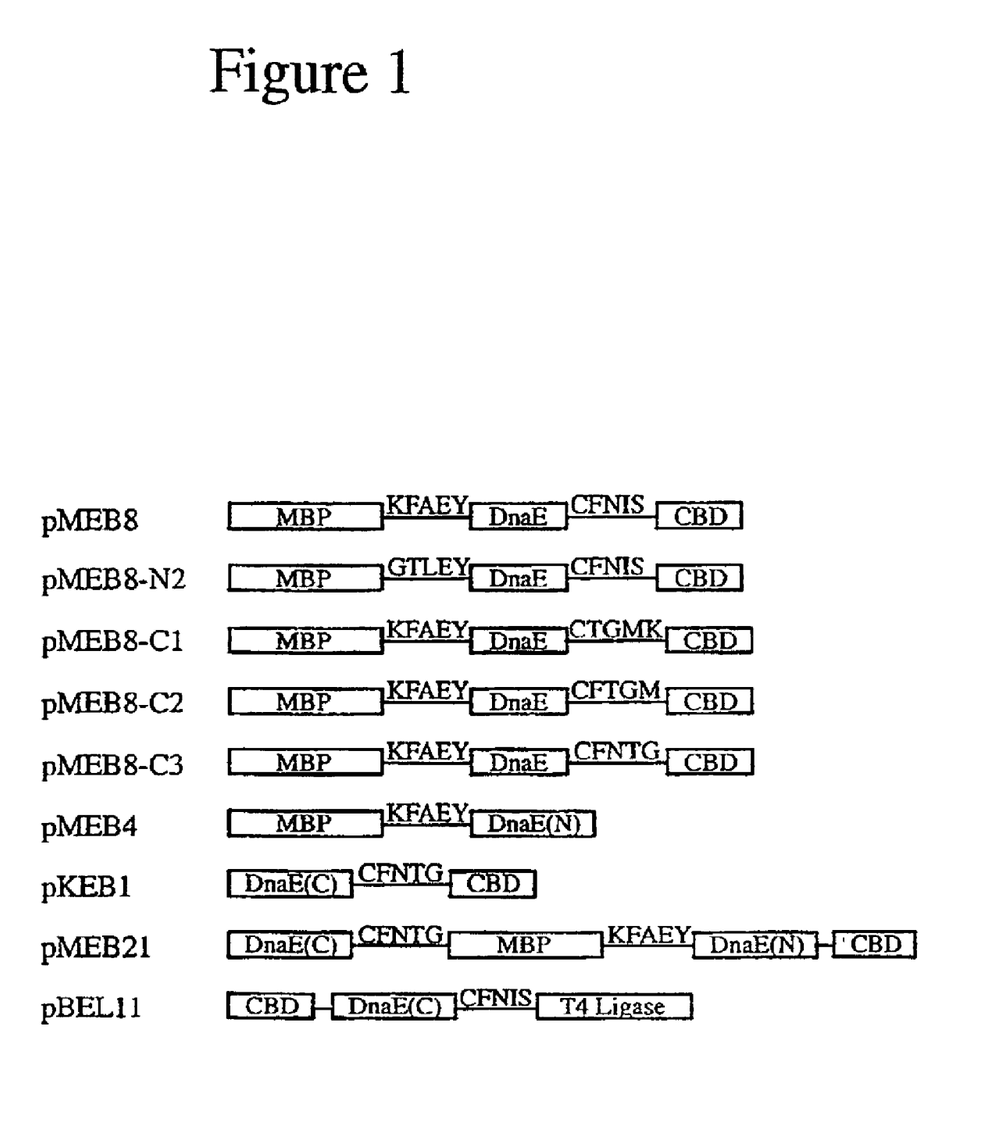
FIG. 1 depicts the Ssp DnaE intein cis- and trans-splicing constructs. The cis-splicing constructs, pMEB8, pMEB8-N2, pMEB8-C1, -C2, and -C3 all use maltose binding protein (MBP) and the chitin binding domain (CBD) as the N- and C-exteins, respectively. The differences are in the extein residues adjacent to the intein and are represented by their single letter code for ease of comparison. The constructs used in the two plasmid, trans-splicing system were pMEB4 and pKEB1 which contain the N- and C-terminal Ssp DnaE intein fragments, DnaE(N) and DnaE(C), respectively. The intramolecular trans-splicing construct, pMEB21, placed DnaE(C) and DnaE(N) at the N- and C-terminus of MBP, respectively.

Creation of Vectors pMEB4, pKEB1, pBEL11, and pMEB8 for trans-splicing studies:

A translation termination codon was introduced into pMEB2 following the codon for Lys$^{123}$ of the Ssp DnaE intein by insertion of a linker formed by annealing oligonucleotides 5'-AAATAAGGAGGTTAATAAAAGGAAGA GCCATGGCGCGCCTTAATTAAA-3' (SEQ ID NO:6) and 5'-CCGGT -TAATTAAGGCGCGCCATGGCTCTTC-CTTTTATTAACCTCCPTA-3' (SEQ ID NO:7). The resulting plasmid, pMEB4, expresses a fusion protein composed of maltose binding protein (MBP) and the N-terminal 123 residues of the Ssp DnaE intein [DnaE(N)]. pKEB1 contains the kanamycin resistance gene and the p15a origin of replication from pACYC177 (Chang and Cohen, *J. Bacteriol.* 134:1141-1156 (1978)). It also expresses a fusion protein composed of the 36 C-terminal amino acids of the Ssp DnaE intein [DnaE(C)] followed by 3 native extein residues and the chitin binding domain (CBD). pBEL11 expresses a CBD-DnaE(C)-T4 DNA ligase fusion protein in the pBSL-C155 vector (Mathys, et al., *Gene* 231:1-13 (1999)).

pMEB8 was generated by transferring the 0.6 kb XhoI to PstI fragment of pMEB3 into pMYB5 (New England Biolabs, Inc. Beverly, Mass.). Mutation of the extein residues in pMEB8 was performed by linker substitutions using the XhoI and KpnI sites flanking the N-terminal splice junction or the NheI and AgeI sites flanking the C-terminal splice junction. pMEB8-N2 retains 2 native N-extein residues while pMEB8-C1, C2, or C3 possess 1, 2 or 3 native C-extein residues (FIG. 1).

Creation of Vector pMEB21 for in vivo and in vitro Cyclization Studies:

The protein cyclization vector, pMEB21, expresses a fusion protein with the DnaE(C) immediately followed by amino acid residues CFNISTG (SEQ ID NO:8), maltose binding protein (MBP), which terminates with amino acid residues GTLEKFAEY (SEQ ID NO:9), and then DnaE(N)-CBD.

EXAMPLE II

The cis-Splicing Activity of the Ssp DnaE Intein in vivo:

The in vivo splicing activity of the full length Ssp DnaE intein was investigated by analyzing protein expression from *E. coli* ER2566 cells (Chong, et al., *Gene* 192(2):271-281 (1997)) bearing plasmid pMEB8. The cells bearing the plasmid were grown in LB medium containing the appropriate antibiotic selection at 37° C. with shaking to an OD$_{600}$ of 0.5. Protein expression was induced by the addition of 0.3 mM Isopropyl β-D-Thiogalactopyranoside (IPTG) at either 15° C. for 16 h or at 37° C. for 2 h. Crude cell extracts were visualized by electrophoresis on a 12% Tris-Glycine gel (Novex, San Diego, Calif.) followed by staining with Coomassie Brilliant Blue.

EXAMPLE III

The Ligation of Two Protein in vivo Using Trans-Splicing:

The in vivo trans-splicing activity of the Ssp DnaE intein was demonstrated by analyzing the proteins from *E. coli* strain ER2566 (Chong, et al., *Gene* 192(2):271-281 (1997)) bearing the two compatible plasmids, pMEB4 and pKEB1. The *E. coli* bearing the plasmids were grown in LB medium containing the appropriate antibiotics (50 µg mL kanamycin and 50 µg/mL ampicillin) at 37° C. with shaking until an OD$_{600}$ of 0.5 was reached. Protein expression was induced by the addition of 0.3 mM Isopropyl B-D-Thiogalactopyranoside (IPTG) at either 15° C. for 16 h or at 37° C. for 2 h. Crude cell extracts were visualized by electrophoresis on a 12% Tris-Glycine gel (Novex, San Diego, Calif.) followed by 5 staining with Coomassie Brilliant Blue.

Protein Purification for in vitro Trans-Splicing or Trans-Cleavage Reactions:

ER2566 cells containing pMEB2 or pBEL11 were grown at 37° C. to an OD $_{600}$ of 0.5. Following IPTG (0.5 mM) induced protein expression overnight at 15° C., cells were harvested by centrifugation at 3,000× g for 30 minutes. The MBP-DnaE(N)-CBD (ME(N)B) fusion protein was purified by amylose as described previously (Evans, et al., *Protein Sci.*, 7:2256-2264 (1998)). The cell pellet was resuspended in Buffer A (20 mM Tris-HCl, pH 7.0 containing 500 mM NaCl) and lysed by sonication. After centrifugation at 23,000× g for 30 minutes the supernatant was applied to a 15 ml amylose resin (New England Biolabs, Inc., Beverly, Mass.) equilibrated in Buffer A. The resin was washed with 10-15 column volumes of Buffer A. The fusion protein was eluted with Buffer B (20 mM Tris-HCl, pH 7.0 containing 500 mM NaCl and 10 mM maltose). Protein concentrations were determined using the Bio-Rad Protein Assay (Bio-Rad Laboratories, Hercules, Calif.).

EXAMPLE IV

In: vitro Trans-Splicing and/or Trans-Cleavage:

Trans-splicing and/or trans-cleavage studies of the Ssp DnaE intein were conducted in vitro using the purified ME(N)B and two 40 amino acid peptides, synthesized as described previously (Evans, et al., Protein Sci. 7:2256-2264 (1998)), consisting of the C-terminal 36 amino acids of the Ssp DnaE intein, with either an Asn (Splice-pep) or an Ala at residue 36 (Cleav-pep), and the next four naturally occurring amino acids (CFNK). The splicing peptide had a biotinylated lysine (K*) as the C-terminal residue. The reaction consisted of adding either the splicing or cleavage peptide (500:M final concentration) to ME(N)B (1 mg/ml) in reaction buffer (100 mM Tris-HCl, pH 7.0 containing 500 mM NaCl) followed by incubation overnight at room temperature. The on-column trans-splicing used the CBD-DnaE (C)-T4 DNA ligase protein absorbed onto a chitin resin in which unbound protein was washed off with 20 column volumes of Buffer A. The ME(N)B fusion protein (9:M), either free in solution or pre-bound to chitin beads, was then added to the chitin bound CBD-DnaE(C)-T4 DNA ligase (3:M). The reactions were then incubated for 16 hours at the appropriate temperature in Buffer A and monitored by SDS-PAGE.

EXAMPLE V

In vitro and in vivo Protein Cyclization Using a Trans-Splicing Intein:

ER2566 cells bearing pMEB21 were grown, induced, harvested and lysed as described in Example II and Example III. The clarified supernatant from cells induced at 15° C. was applied to an amylose resin (10 mL bed volume) whereas the clarified supernatant from cells induced at 37° C. was applied to a chitin resin (15 mL bed volume). Unbound proteins were washed from the resin with 20 column volumes of Buffer A. Proteins were eluted from the amylose column with Buffer B. The intramolecular trans-splicing reaction proceeded in vitro when the chitin column was incubated for 20 hours at room temperature. Reaction products were eluted from the resin with Buffer A. The cyclic maltose binding protein (MBP) was analyzed by treatment with Factor Xa (Fxa) (1:100, FXa:protein mass to mass ratio) overnight at 4° C. to generate linearized MBP. The proteolyzed proteins were subjected to amino acid sequencing using a Procise 494 protein sequencer (PE Applied Biosystems, Foster City, Calif.).

EXAMPLE VI

Figure 2:
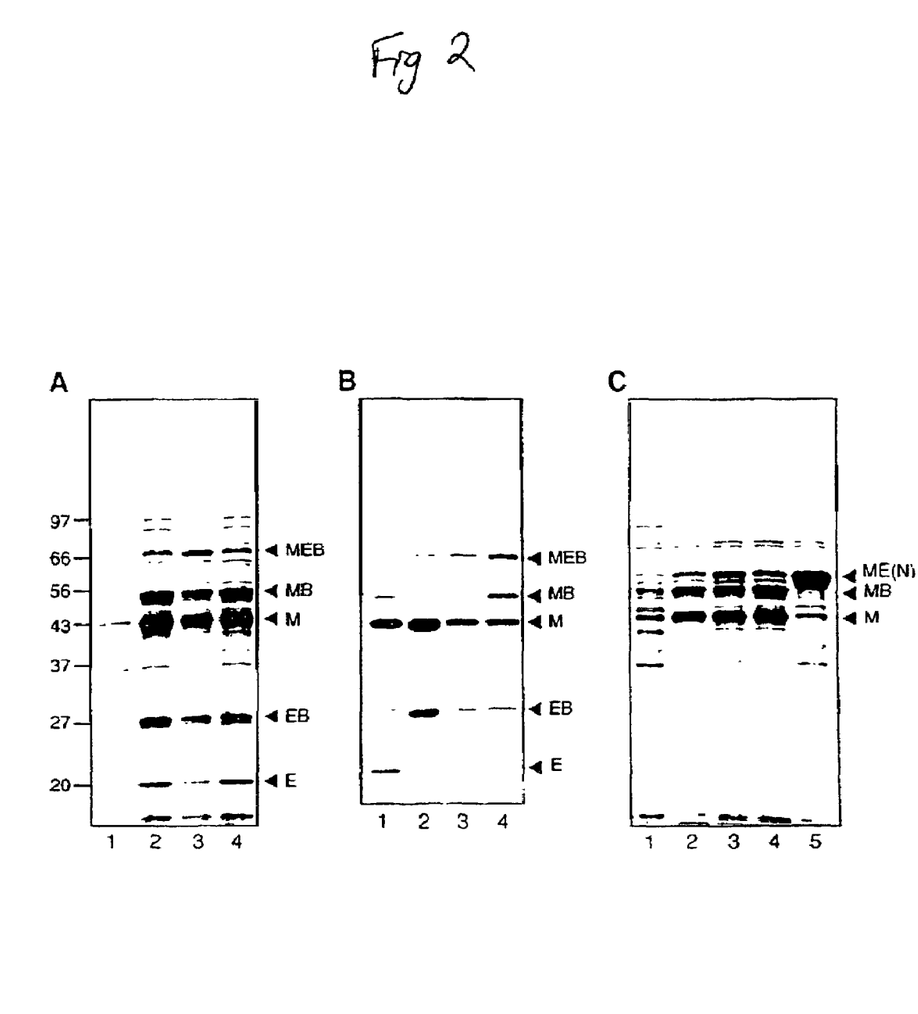
FIG. 2 is a gel depicting the in vivo splicing of the Ssp DnaE intein by SDS-PAGE.

The Ligation of Maltose Binding Protein and the Chitin Binding Domain using a cis-Splicing Intein A gene fusion was created in which full length Ssp DnaE intein had maltose binding protein (MBP, 42 kDa) fused to its N-terminus and the chitin binding domain fused to its C-terminus. This fusion protein was expressed from the from the ER2566 cells bearing plasmid pMEB8 as described in FIG. 1 and in Example II and Example III above. A band corresponding to the ligation of maltose binding protein and the chitin binding domain (MBP-CBD) (MB) following induction of protein expression demonstrated that the Ssp DnaE intein can splice in cis with only 5 native N-terminal and 3 native C-terminal extein residues (FIG. 2A, lane 2). The identity of splicing products was confirmed by western blot analysis using anti-maltose binding protein (anti-MBP) and anti-chitin binding domain (anti-CBD) antibodies and binding to chitin and amylose resins (data not shown). In addition to the spliced product, there was significant cleavage of the peptide bond at the N-terminus of the Ssp DnaE intein.

EXAMPLE VII

Alteration of cis-Splicing by Changing the Amino Acids Adjacent to the Intein

The amino acids adjacent to the intein (the extein amino acid residues) were changed by mutation in the cis-splicing construct (FIG. 2B). Splicing products were detected upon induction of ER2566 E. coli cells bearing plasmids pMEB8, pMEB8-N2, or pMEB8-C3 as described in Example I above. These results demonstrated that splicing could occur with either 2 proximal N-extein residues or 3 proximal C-extein residues (FIG. 1 and FIG. 2B, lanes 1 & 4). However, analysis of protein expression following induction of ER2566 E. coli cells bearing plasmids pMEB8-C1 or pMEB8-C2 as described above in Example I did not detect any MBP-CBD fusion protein. This demonstrated that splicing activity could be altered by reduction of the C-extein sequence to 1 or 2 native amino acid residues (FIG. 2B, lanes 2 & 3).

EXAMPLE VIII

Temperature Dependent Trans-Splicing of the Ssp DnaE Intein

The extent of in vivo trans-splicing varied depending on the temperature of the E. coli cell growth during induction of protein expression. E. coli ER2566 bearing plasmids pMEB4 and pKEB1 were induced to express protein as described above in Example II. The temperature at which the E. coli cells were incubated following induction was either 37° C. or 15° C. There was an accumulation of Ssp DnaE intein precursor protein when protein expression was induced at 37° C. and this was processed after further growth overnight at 15° C. (FIG. 2A and FIG. 2C).

EXAMPLE IX

The Ligation of two Ribosomally Expressed Proteins in vitro Using the Trans-Splicing Ssp DnaE Intein.

Figure 4A:
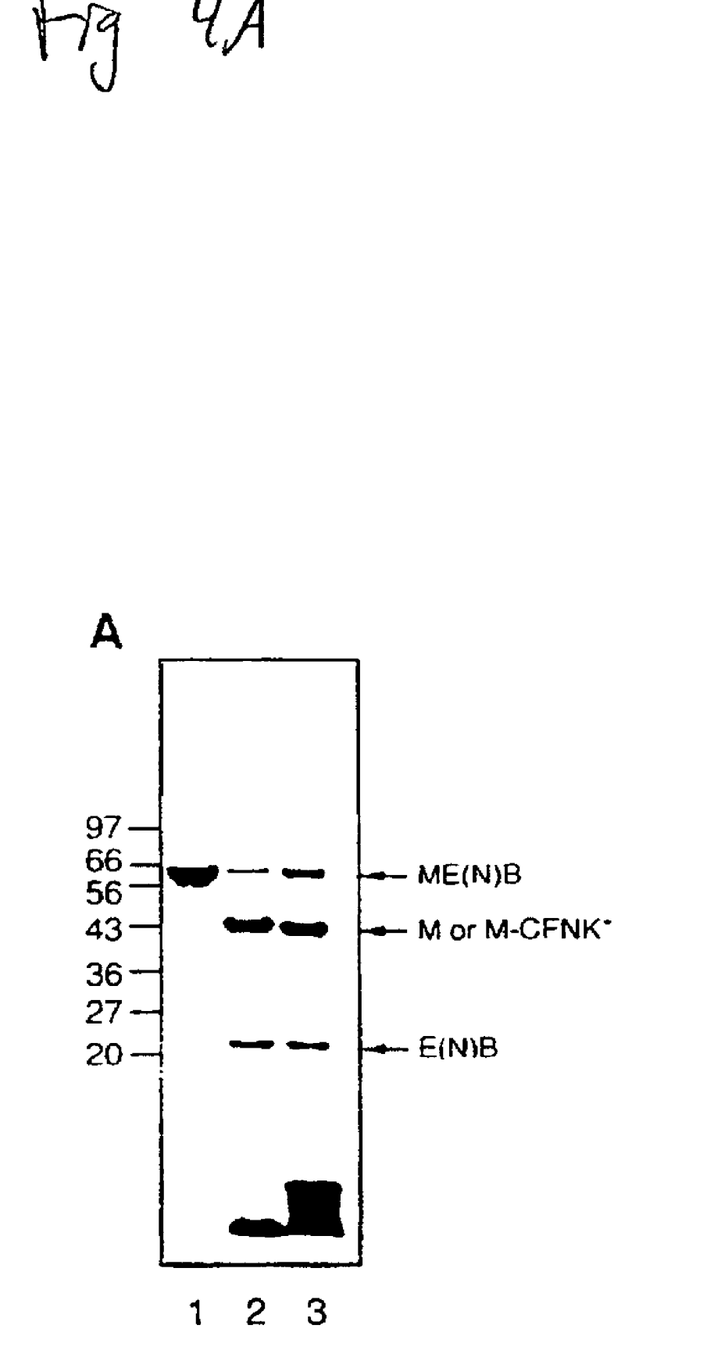
Figure 4B:
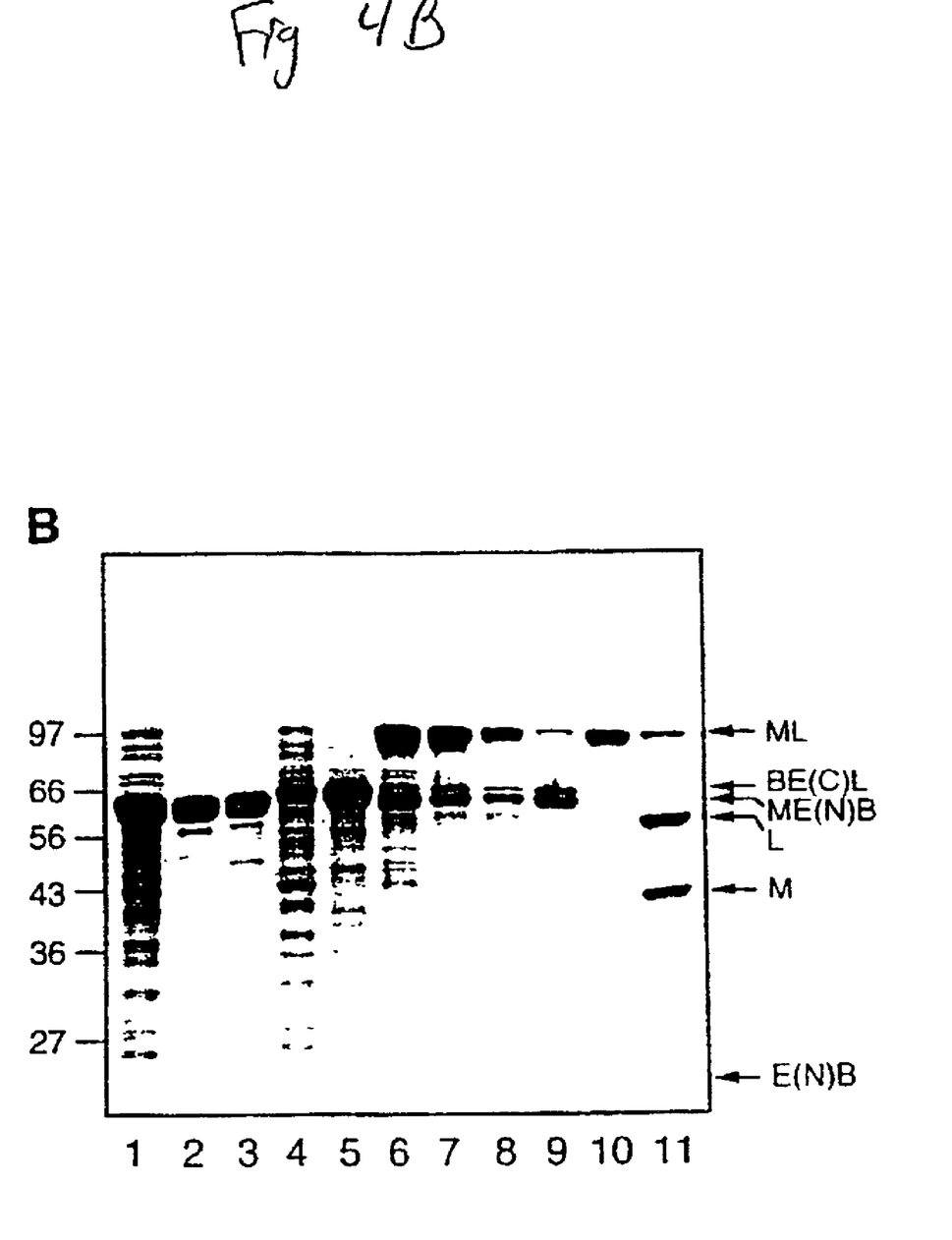

Maltose binding protein was ligated to T4 DNA ligase by first purifying Maltose binding protein fused to the N-terminus of the N-terminal splicing domain of the Ssp DnaE intein. The chitin binding domain was present as an in-frame fusion to the C-terminus of the Ssp DnaE intein N-terminal splicing domain. This fusion protein is expressed from plasmid pMEB8 as described in Example II and is abbreviated MBP-DnaE(N)-CBD. T4 DNA ligase was purified separately as a fusion to the C-terminus of the C-terminal splicing domain of the Ssp DnaE intein. The chitin binding domain was present as an in-frame fusion to the N-terminus of the Ssp DnaE intein C-terminal splicing domain. This fusion protein is expressed from plasmid pBEL11 and is abbreviated CBD-DnaE(C)-T4 DNA ligase. These two proteins were bound to a chitin resin through the chitin binding domain regions. Efficient in vitro trans-splicing occurred between the two bacterially-expressed proteins, MBP-DnaE (N)-CBD and CBD-DnaE(C)-T4 DNA ligase, yielding spliced product, MBP-T4 DNA Ligase (ML), at 4° C. and 16° C. but significantly less at 37° C. (FIG. 4B). Little difference in splicing efficiency was observed when either chitin bound or free ME(N)B was used to react with the chitin bound BE(C) ligase. Following Factor Xa (Fxa) proteolysis of the released ligation product, amino acid sequencing of the 58 kDa band (expected for T4 DNA ligase) yielded NH$_2$-GTLEKFAEYCFNIST-COOH (SEQ ID NO:10) which corresponds to the expected sequence of the splice junction.

EXAMPLE X

In vitro Trans-Cleavage or Trans-Splicing Using a Synthetic Peptide

Figure 3:
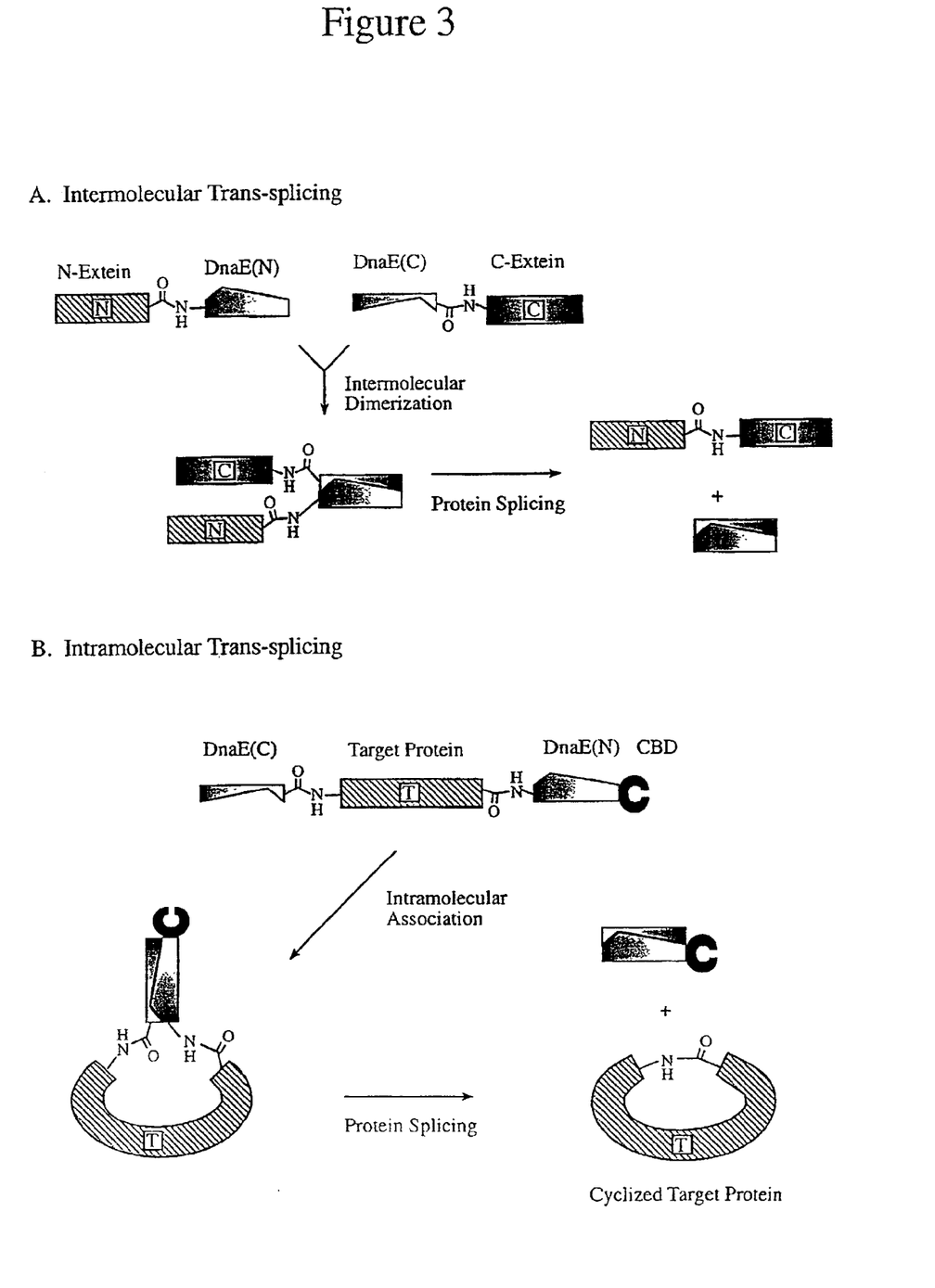
FIG. 3 is a gel depicting protein trans-splicing and cyclization reactions using the Ssp DnaE intein.

The In vitro trans-splicing (FIG. 3) and/or trans-cleavage activity of the Ssp DnaE intein was demonstrated using the bacterially-expressed ME(N)B precursor and 2 peptides, Splice-pep and Cleav-pep, that mimic the C-terminal Ssp DnaE intein fragment (see Example IV above). Both the Splice-pep and the Cleav-pep could activate ME(N)B, resulting in bands corresponding to the expected spliced and/or cleavage product (FIG. 4A). Furthermore, the ME(N)B precursor was stable in the absence of either peptide FIG. 4A, lane 1). The cleavage and splicing products, maltose binding protein (MBP) and MBP-CFNK*, respectively, are indistinguishable by SDS-PAGE. However, a western blot using anti-biotin antibody indicated that splicing was occurring, albeit the extent of reaction could not be determined (data not shown).

EXAMPLE XI

In vivo Protein Cyclization using the Ssp DnaE Intein

Maltose binding protein was cyclized both in vitro and iii vivo using the Ssp DnaE intein. The C-terminus of the C-terminal Ssp DnaE intein splicing domain was fused to the N-terminus of maltose binding protein and the N-terminus of the N-terminal Ssp DnaE intein splicing domain was fused to the C-terminus of the same maltose binding protein. The N-terminal splicing domain of the Ssp DnaE intein also had the chitin binding domain fused in-frame to its C-terminus. This fusion protein, abbreviated DnaE(C)MBP-DnaE(N)-CBD, was expressed in E. coli ER2566 cells bearing plasmid pMEB21 as described in Example V above. Following induction of the cells bearing plasmid pMEB21 the crude cell lysate was analyzed by SDS-PAGE (FIG. 5A, lane 2) and western blot analysis and demonstrated that cells expressing pMEB21 contained precursor protein, DnaE(C) MBP-DnaE(N)-CBD, linear MBP, circular MBP, DnaE(N)-CBD, and DnaE(C)MBP. The putative linear and cyclic MBP species as well as higher molecular weight species (FIG. 5A, lane 4) were found to bind to amylose and elute with maltose.

EXAMPLE XII

In vitro Protein Cyclization using the Ssp DnaE Intein

Figure 5:
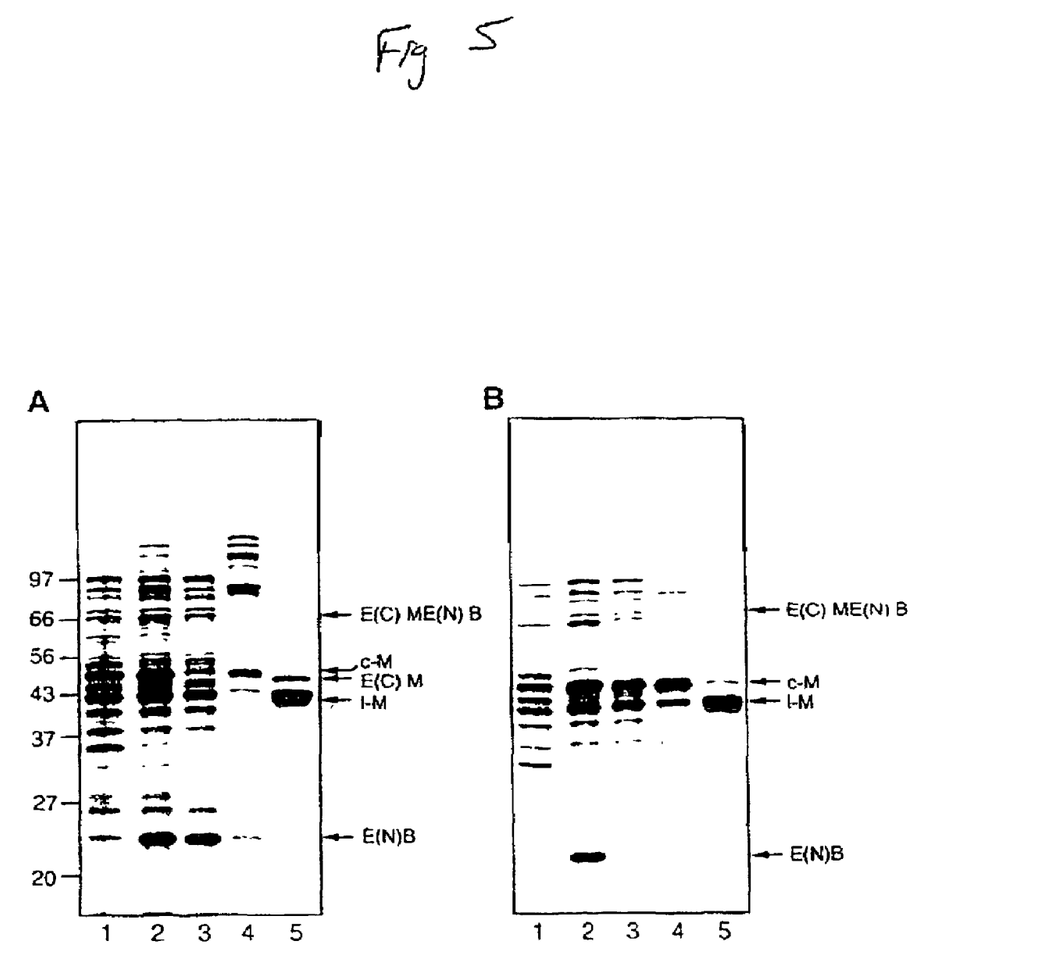
FIG. 5 is a gel depicting protein circularization in E. coli and on a chitin column using the intein based technologies described in the present patent application.

In vitro cyclization was performed by isolating the precursor consisting of DnaE(C)-MBP-DnaE(N)-CBD which could be obtained by inducing protein expression of E. coli ER2566 bearing plasmid pMEB21 for 2 hours at 37° C. (FIG. 5B, lane 2) as described in Example V above. The crude cell lysate was applied to a chitin resin to which the precursor bound through the CBD. Unbound proteins were washed from the column and the cyclization reaction proceeded overnight at 23° C. Fractions from the chitin resin contained cyclic and linear MBP species (FIG. 5B, lane 4). Factor Xa (Fxa) treatment of the isolated proteins (FIG. 5B, lane 5) followed by amino acid sequencing confirmed the presence of both the linear and circular forms.

EXAMPLE XIII

Amino acid sequencing of the ligation junction of cyclic MBP

The maltose eluted proteins were subjected to Factor Xa (Fxa) proteolysis and amino acid sequencing. The upper portion of the 43 kDa band yielded NH$_2$-G TLE-KFAEYXFNISTGM-COOH (SEQ ID NO: 11) which matched the sequence for the cyclic maltose binding protein (MBP) that was linearized with Factor Xa (Fxa). Sequencing the lower part of the 43 kDa band gave NH$_2$-XFNISTGM-COOH (SEQ ID NO: 12) which matched the N-terminus of the linear maltose binding protein (MBP) which had not undergone cyclization. NH$_2$-XVKIG RRSLGV-COOH (SEQ ID NO:13) was obtained from the 45 kDa band and correlates with the expected sequence from the DnaE(C)-MBP product. The X designates a sequencing cycle in which no amino acid could be assigned with confidence.

What is claimed is:

1. A method for producing a fused polypeptide, comprising: the steps of:
    (a) immobilizing a first polypeptide or portion thereof fused to a first intein fragment on a solid support;
    (b) adding a second polypeptide or portion thereof fused to a second intein fragment to (a) wherein said second intein fragment is complementary to said first intein fragment; and
    (c) reacting the first and the second polypeptides under conditions which favor transplicing of said first and second polypeptides to produce a fused polypeptide comprising said first and second polypeptides.

2. The method of claim 1, further comprising the step of eluting the fused polypeptide from the solid support.

3. The method of claim 1, wherein said first and second polypeptides are selected from the group consisting of peptides, proteins and enzymes.

4. The method of claim 1, wherein said solid support is selected from the group consisting of affinity based supports, chips, plates, biochip supports, glass wafers and microtiter plates.

5. The method of claim 1, wherein the first and second intein fragments are selected from the group consisting of naturally split inteins and artificially split inteins.

6. The method of claim 5, wherein said first and second intein fragments are obtained from an intein selected from the group consisting of the Ssp DnaE intein, Ssp DnaB intein, Mtu RecA intein, Psp Pol-I intein, PI-pful intein and PI-pfull intein.

7. The method of claim 1, wherein the first and second intein fragment further comprised an affinity binding domain.

8. The method of claim 7, wherein the affinity binding domain is selected from the group consisting of the chitin binding domain from B. circulans, the maltose binding protein from E. coli, a His tag, cellulose binding protein and a Flag-tag.

9. The method of claim 1, wherein said first polypeptide comprises an N-terminal intein fragment fused to the C-terminus of said first polypeptide.

10. The method of claim 1, wherein said second intein fragment comprises a C-terminal intein fragment fused to the N-terminus of said second polypeptide.

11. A method for producing a cyclic polypeptide, comprising the steps of:
- (a) fusing the C-terminal portion of a split intein to the N-terminus of a target polypeptide and fusing the N-terminal portion of a split intein to the C-terminus of said target polypeptide to produce a fused polypeptide;
- (b) fusing an affinity binding domain to said fused polypeptide;
- (c) immobilizing the product of step (b) on a solid support; and
- (d) incubating the immobilized precursor under conditions that favor formation of the cyclic polypeptide to form the cyclic polypeptide.

12. A method for the in viva production of a cyclic polypeptide comprising the steps of:
- (a) fusing the C-terminal portion of a split intein to the N-terminus of a target polypeptide and fusing the N-terminal portion of a split intein to the C-terminus of said target polypeptide to produce a fused polypeptide; and
- (b) reacting said fused polypeptide in viva under conditions favoring the formation of a cyclic polypeptide.

13. The method of claim 11, further comprising the step of eluting said cyclic polypeptide from said solid support.

14. The method of claims 11 or 12, wherein the target polypeptide is selected from the group consisting of a peptide, a protein and an enzyme.

15. The method of claim 11, wherein said solid support is selected from the group consisting of affinity based supports, chips, plates, biochip supports, glass wafers and microtiter plates.

16. The method of claims 11 or 12, wherein said split intein is a naturally split intein.

17. The method of claim 11, wherein said split intein is an artificially split intein.

18. The method of claim 11, wherein the affinity binding domain is selected from the group consisting of the chitin binding domain, the maltose binding protein, a His tag, the cellulose binding protein and a Flag-tag.

19. A method for the in vivo production of a cyclic polypeptide comprising the steps of:
- (a) fusing the C-terminal portion of an artificially split intein to the N-terminus of a target polypeptide and fusing the N-terminal portion of the artificially split intein to the C-terminus of said target polypeptide to produce a fused polypeptide; and
- (b) reacting said fused polypeptide in vivo under conditions favoring the formation of a cyclic polypeptide.

20. A method according to claim 1, wherein the second polypeptide is immobilized.

* * * * *

UNITED STATES PATENT AND TRADEMARK OFFICE
CERTIFICATE OF CORRECTION

| | | |
|---|---|---|
| PATENT NO. | : 7,271,256 B2 | Page 1 of 1 |
| APPLICATION NO. | : 09/937070 | |
| DATED | : September 18, 2007 | |
| INVENTOR(S) | : Thomas C. Evans, Jr. et al. | |

It is certified that error appears in the above-identified patent and that said Letters Patent is hereby corrected as shown below:

In the specification

At column 1, line 21, change "posses" to --possess--

At column 7, line 13, change "it's" to --its--

At column 8, line 46, change "trans-splicin" to --transplicing--

At column 12, line 41, change "Protein" to --Proteins--

At column 13, line 11, change "In:" to --In--

At column 15, line 16, change "In" to --in--

At column 15, line 36, change "iii" to --in--

In the claims

At column 17, claim number 12, line 14, change "viva" to --vivo--

At column 17, claim number 12, line 21, change "viva" to --vivo--

Signed and Sealed this
Twenty-ninth Day of November, 2011

David J. Kappos
*Director of the United States Patent and Trademark Office*